United States Patent [19]

Nakaji et al.

[11] Patent Number: 4,913,860
[45] Date of Patent: Apr. 3, 1990

[54] METHOD OF USING PORCELAIN BLOCK IN PORCELAIN PRESS TECHNIQUE FOR DENTAL USE

[76] Inventors: Naotaka Nakaji; Kisao Nakaji, both of Hayashi-Bldg. #201, 7-8, Nishikigaoka, Kumamoto-shi, Japan

[21] Appl. No.: 224,226

[22] Filed: Jul. 22, 1988

Related U.S. Application Data

[63] Continuation of Ser. No. 5,273, Jan. 20, 1987, abandoned.

[51] Int. Cl.$^4$ ............... A61C 13/00; A61C 13/20; B28B 1/00
[52] U.S. Cl. .................. 264/16; 264/17; 264/138
[58] Field of Search .............. 264/16, 17, 18, 19, 264/138; 501/141

[56] References Cited

U.S. PATENT DOCUMENTS

| | | | |
|---|---|---|---|
| 1,370,192 | 3/1921 | Crate | 264/19 |
| 1,382,010 | 6/1921 | Nishi | 264/19 X |
| 2,249,890 | 7/1941 | Dioge | 264/19 X |
| 2,550,938 | 5/1951 | Raber | 264/19 |
| 3,562,365 | 2/1971 | Redgwell | 264/16 |
| 3,649,732 | 3/1972 | Brigham et al. | 264/16 X |
| 3,973,970 | 8/1976 | Mabie | 501/141 X |
| 4,378,248 | 3/1983 | Griffith | 264/16 X |
| 4,381,918 | 5/1983 | Ehrnford | 264/16 X |
| 4,585,417 | 4/1986 | Sozio et al. | 264/19 X |

OTHER PUBLICATIONS

Slocum, "The Technic of Porcelain Jacket Crowns and the Relationship to Peridontics", Dental Digest, Oct. 27, 1924.
Droge, G. G. J., "Possibilities for Use of Ceramic Material in Conventional Methods and in the Porcelain Press Method, Parts I, II and III" (Translated Title), Die Quintessenz, No. 5, pp. 67-73, No. 6, pp. 39-46, No. 7, pp. 35-42, 1979 (Translation included).
McPhee, E. Richard, "Hot—Pressed Porcelain Process for Porcelain—Fused—To—Metal Restorations", The Journal of Prosthetic Dentistry, vol. 33, No. 5, pp. 577-581, 1975.
McPhee, E. Richard, "Hot Compressed Porcelain Process for Ceramo—Metal Restorations", pp. 245-250, Approx. 1975.
Whip Mix Corporation, sundry brochures, 4 pp., 1985-1986.
Dentsply International Inc., "Shademate Porcelain Laminate Veneers", Jan. 1986.
Nakaji, Naotaka, "The Applied Technique When Porcelain Block is Used For Porcelain Press Technique", Unpublished Copyright Registration TXu—275—786, Mar. 12, 1987.

Primary Examiner—Jan H. Silbaugh
Assistant Examiner—Karen D. Kutach
Attorney, Agent, or Firm—Volpe and Koenig

[57] ABSTRACT

A homogeneous porcelain block is used instead of using porcelain powder in a porcelain press technique to make dental prosthesis. Porcelain block is placed directly onto a mold, and softened by heating. Then the upper and the lower flasks of the mold assembly are closed so as to press the porcelain block. The process prevents adverse effects from steam and gases during the procedure. Therefore the porcelain block eliminates discoloration, bubbles, uneven baking and weakness in the porcelain block. In addition, considerable time and labor may be saved.

6 Claims, 1 Drawing Sheet

METHOD OF USING PORCELAIN BLOCK IN PORCELAIN PRESS TECHNIQUE FOR DENTAL USE

This application is a continuation of U.S. patent application Ser. No. 005,273 filed Jan. 20, 1989, now abandoned.

FIELD OF INVENTION

This invention relates to the manufacture of dental prosthesis, and in particular to a porcelain press technique for use in making dental porcelain prosthetic appliances easily and efficiently.

BACKGROUND—DESCRIPTION OF PRIOR ART

The use of porcelain in the manufacture of dental prosthesis such as caps, bridge work, etc. is well known in the art. Dental grade porcelain products provide strong durable dental restorations which can closely match natural teeth in appearance. In the creation of dental prosthesis, it is well known to create a selectively configured mold dividing it into upper and lower flask portions. Dental prosthesis mold are generally made from investment material such as V.H.T. Industrial Investment available from the Whip Mix Corp., Louisville, Ky. If the porcelain can be pressed into the mold without problems, the fabrication of porcelain prosthetic appliances can be made easily and efficiently.

In conventional porcelain press techniques, it is common to use porcelain powder.

First, the investment is degassed. This process entails drying the mold to release ammonia gas. If the mold is not degassed, ammonia or other gas may be released during the pressing process which can cause bubbles to form within the molded prosthesis. After degassing, the lower flask is soaked in water to permit the investment to absorb sufficient water. Next, the water/porcelain powder mixture is poured into the mold and then condensed by vibrating the flask. Excess water coming up to the surface by vibration may be removed by blotting with tissue paper. The process is repeated until excess water does not emerge. After water is completely removed from the porcelain and investment; the flasks are placed in the muffle of a furnace; the upper and lower flasks being assembled in preparation of the pressing operation. Porcelain powder is fired according to the porcelain manufacturer's recommended guidelines. The temperature is then increased (about 100° C. higher than firing temperature) so as to soften the porcelain under air pressure. The flask halves are then closed pressing the porcelain into the mold cavity.

Users regarded this method as unsatisfactory for porcelain press technique, because of the following:

porcelain powder in the mold may not be condensed properly, because water from the mixture is likely to be absorbed into the investment during the procedure of condensation;

porcelain powder may be dispersed by steam or gases grom the mold while it is being dried;

removal of water from porcelain powder and investment is very time consuming;

white color may appear in the porcelain around the porcelain excess area after pressing;

discoloration and bubbles may occur in the porcelain, brought about by steam and gases during the process; and uneven baking of the porcelain may occur within the mold during the firing.

The significant difference in the degree of softness in the porcelain at the surface of the mold and within the interior of the mold, while the firing is being performed, is a contributing factor towards unsatisfactory pressing of porcelain into the required detail.

From the above, it is seen that porcelain powder used in porcelain press techniques creates unnecessary problems leading to inefficiency in time and labor. Numerous attempts have been made in the past to find a satisfactory solution to the problems, but without success.

OBJECTS AND SUMMARY OF THE INVENTION

It is the object of the invention (1) to provide a porcelain press technique for use in making dental prosthetic appliances easily and efficiently through the use of porcelain block;

(2) to provide a method for easy, reliable and neat pressing of porcelain for various types of dental porcelain prosthetic appliances;

(3) to provide a method which can eliminate several disadvantages at the same time;

(4) to provide a method which requires minimum skill and training to use;

(5) to provide a method which can do a complete job of porcelain pressing without requiring condensation of porcelain powder in the mold and without degassing of the investment in advance;

(6) to provide a method which eliminates discoloration, bubbles, uneven baking and weakness in the porcelain; and (7) to provide a method in which the porcelain can be pressed into the required detail.

The process entails use of a porcelain block, in which the particles of porcelain have been fused together, to prevent adverse effects from steam and gases. Therefore, porcelain block does not have discoloration and bubbles which cause the weakness of porcelain. Accordingly, the porcelain block may be pressed into the detail of the mold, because porcelain has been maked evenly in advance.

The porcelain block is placed within the mold cavity between the open upper and lower flask halves of the mold assembly and the entire assembly is placed in the muffle of a furnace. There are two ways to press porcelain block into the mold.

The first press method is to use the conventional pressing technique for powdered porcelain which was originally devised by Dr. G. G. J. Dröge and has been adapted for use in specially designed porcelain furnaces which are well known in the art. Such furnaces use a metal rod from outside of the muffle and lift up the assembly (6) in FIG. 1 to the upper wall of the muffle, and close the upper flask and lower flask under high temperature in the muffle, then pressing the porcelain block into the mold in the assembly (6).

Another pressing method is to use a hand press. The assembly is removed from the muffle after the porcelain block has become soft, and is placed on hand press. Then, the upper and lower flasks are closed on the press by pushing down with the handle without delay at room temperature. The porcelain block is thereby compressed in the mold.

Other objects and advantages of the invention will be apparent from a consideration of the ensuing description and the accompanying drawings.

DETAILED DESCRIPTION OF A PREFERRED EMBODIMENT

Figure 1:
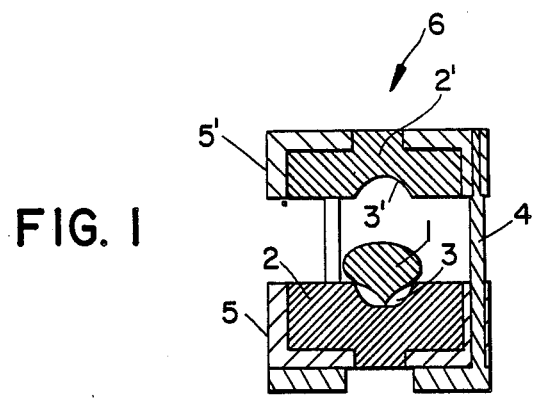
FIG. 1 is a side sectional view of the flasks with the investment filled inside.

Referring to FIG. 1, there is shown a mold assembly (6) having lower and upper flasks (5,5') and guide posts (4) which project from the bottom of the mold assembly (6).

A mold cavity (3) is defined in the lower flask (5) within investment material (2). A mold cavity (3') is defined in the upper flask (5') within investment material (2'). The upper flask (5') is supported by the guide posts (4).

Figure 2:
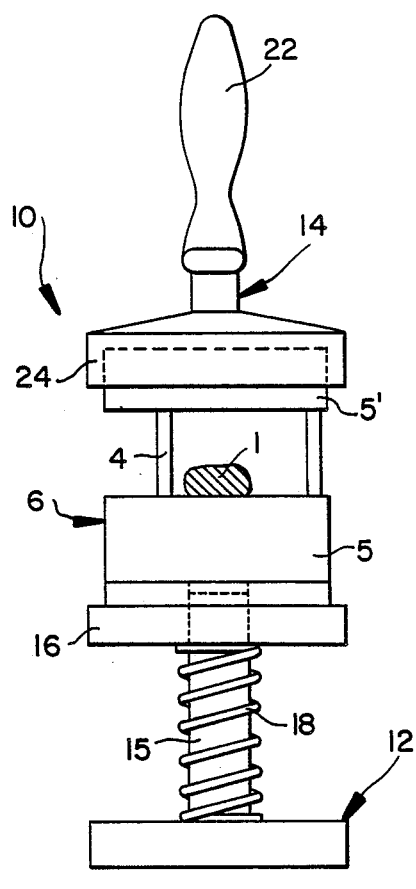
FIG. 2 is a side view showing the flasks on the press, where the flasks have been removed from the muffle after porcelain block has become soft.
Figure 3:
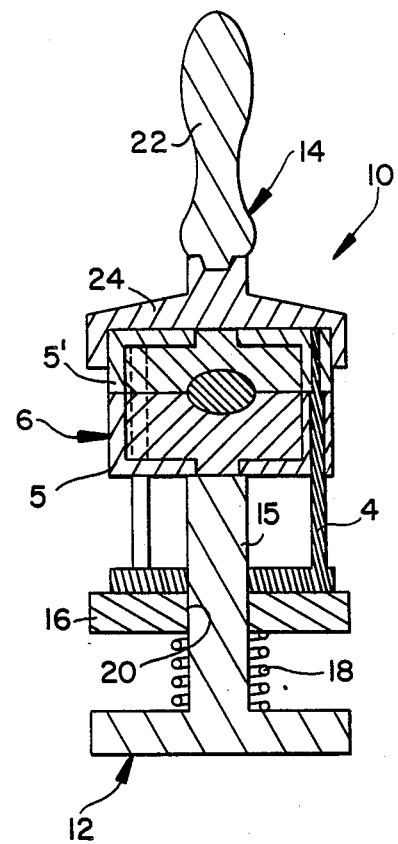
FIG. 3 is a side sectional view and it shows the porcelain block being pressed into the mold cavities.

Referring to FIGS. 2 and 3, a hand press (10) is disclosed having a base (12) and a top (14). The base includes a support post (15). A platform (16) is suspended above the base (12) on a spring (18) located about support pillar (15). The platform is selectively configured to receive the bottom of the mold assembly (6) having an opening (20) therein through which the support post (15) projects for engagement with the bottom flask (5) of the mold assembly (6).

The top piece of the press (14) includes a handle (22) which is fixed to a cap (24) which is selectively configured for engagement with the top of the mold assembly.

A block of porcelain material is prepared by mixing dental grade porcelain powder with water in accordance with the manufacturer's directions and then evenly baking the porcelain powder mixture to fuse the particles of porcelain together.

In operation, the user first cuts and adjusts the porcelain block (1) onto the mold (3), and makes it stable onto the mold (3) in the lower flask (5). Then the assembly (6) with the porcelain block (1) is placed in the muffle of a furnace so as to soften the porcelain block (1). The porcelain block (1) is rendered soft for pressing at about 100° C. above the firing temperature (i.e. firing temperature recommended by porcelain powder manufacturer).

The mold assembly (6) is removed from the muffle after the porcelain block (1) has become soft and is placed in the hand press (10). The upper and lower flasks (5', 5) are closed on the press (10) by pushing down on the handle (14) without delay at room temperature. The porcelain block is thereby compressed into the mold.

Alternatively, a conventional porcelain furnace having a in situ press mechanism may be employed to press the flask halves together while within the muffle of the furnace after the porcelain block has been softened.

The user will find advantages of using porcelain block used in porcelain press technique for making and porcelain prosthetic appliances.

User can also use the porcelain block for making porcelain prosthetic appliances with different types of porcelain materials.

While the above description contains many specificities, the reader should not construe these as limitations on the scope of the invention, but merely as exemplifications of preferred embodiments thereof. Many other possible variations that are within its scope can be envisioned.

For example, users are able to fabricate porcelain fused metal crowns and bridges, porcelain jacketed crowns, porcelain inlay, porcelain veneer, porcelain denture tooth, and the like.

We claim:

1. A process for manufacturing dental prosthesis:
    providing a mold assembly including upper and lower flasks having a selectively configured mold cavity defined in investment material therein;
    preparing a homogeneous block of porcelain material in advance by baking porcelain powder to fuse together particles of said porcelain powder;
    cutting and placing said preformed homogeneous block of porcelain material onto said lower flask such that said cutting of said porcelain block facilitates stable placement of said block onto said lower flask;
    heating said mold assembly having said porcelain block on said lower flask until said porcelain block is heated to approximately 100° C. above the firing temperature of said porcelain material thereby softening said porcelain block; and
    pressing said softened porcelain block into said mold cavity to form said dental prosthesis.

2. A process as defined in claim 1, in which said porcelain block is prepared from porcelain powder which has been baked evenly in advance.

3. A process according to claim 1 wherein said mold assembly and said porcelain block are heated within a furnace and are removed from said furnace whereafter said pressing is conducted at room temperature without delay.

4. A process according to claim 3 further comprising:
    providing a hand press for pressing said upper and lower flasks together to press said softened porcelain block into said mold cavity.

5. In an improved process of manufacturing porcelain dental prosthesis wherein a selectively configured mold cavity is defined in investment material in upper and lower flasks of a mold assembly, an amount of porcelain material is placed in the lower flask cavity portion sufficient to fill the entire cavity, and said mold assembly with said porcelain material disposed within said lower flask cavity portion is placed in the muffle of a furnace, the improvement comprising:
    preforming said porcelain material into a homogenous block of porcelain material by fusing together particles of a porcelain powder during baking of said porcelain powder, and cutting and placing said preformed porcelain block in said lower flask cavity portion;
    heating said mold assembly and porcelain block within said muffle until said porcelain block is heated to approximately 100° C. above the firing temperature of said porcelain material thereby softening said block of porcelain material;
    removing said mold assembly and said porcelain block from said muffle; and
    closing said flasks of said mold assembly together without delay at room temperature thereby deforming said softened porcelain block to fill said mold cavity and form said dental prosthesis.

6. A process according to claim 5 further comprising: providing a hand press for closing said flasks.

* * * * *

UNITED STATES PATENT AND TRADEMARK OFFICE
CERTIFICATE OF CORRECTION

PATENT NO. : 4,913,860

DATED : April 3, 1990

INVENTOR(S) : Naotaka Nakaji, et al

It is certified that error appears in the above-identified patent and that said Letters Patent is hereby corrected as shown below:

Column 1, line 61, delete the word "grom" and insert therefor --from--.

Column 2, line 42, delete the word "maked" and insert therefor --baked--.

Signed and Sealed this

Nineteenth Day of February, 1991

Attest:

HARRY F. MANBECK, JR.

Attesting Officer

Commissioner of Patents and Trademarks